United States Patent
Tsuji et al.

(10) Patent No.: US 8,420,073 B2
(45) Date of Patent: Apr. 16, 2013

(54) EQUOL-PRODUCING BACTERIUM AND USE THEREOF

(75) Inventors: Hirokazu Tsuji, Minato-ku (JP); Koji Nomoto, Minato-ku (JP); Kaoru Moriyama, Minato-ku (JP); Hideyuki Akaza, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/203,144

(22) PCT Filed: Feb. 25, 2010

(86) PCT No.: PCT/JP2010/001272
§ 371 (c)(1),
(2), (4) Date: Aug. 24, 2011

(87) PCT Pub. No.: WO2010/098103
PCT Pub. Date: Sep. 2, 2010

(65) Prior Publication Data
US 2011/0318309 A1 Dec. 29, 2011

(30) Foreign Application Priority Data
Feb. 25, 2009 (JP) ................................. 2009-042867

(51) Int. Cl.
*A01N 63/00* (2006.01)
*C12N 1/12* (2006.01)
*C12N 1/20* (2006.01)

(52) U.S. Cl.
USPC ...................................... 424/93.4; 435/252.1

(58) Field of Classification Search ........................ None
See application file for complete search history.

(56) References Cited

U.S. PATENT DOCUMENTS

| | | | |
|---|---|---|---|
| 6,716,424 | B1 | 4/2004 | Uchiyama et al. |
| 2004/0141954 | A1 | 7/2004 | Uchiyama et al. |
| 2004/0147594 | A1 | 7/2004 | Setchell et al. |
| 2004/0235758 | A1 | 11/2004 | Setchell et al. |
| 2006/0148045 | A1 | 7/2006 | Uchiyama et al. |
| 2008/0131412 | A1 | 6/2008 | Uchiyama et al. |
| 2009/0018185 | A1 | 1/2009 | Setchell et al. |
| 2009/0253643 | A1 | 10/2009 | Tsuji et al. |
| 2010/0076071 | A1 | 3/2010 | Lephart et al. |
| 2010/0120705 | A1 | 5/2010 | Setchell et al. |

FOREIGN PATENT DOCUMENTS

| | | |
|---|---|---|
| JP | 2006 504409 | 2/2006 |
| JP | 2006 204296 | 8/2006 |
| WO | 99 07392 | 2/1999 |
| WO | 2005 000042 | 1/2005 |

OTHER PUBLICATIONS

Jin et al, International Journal of Systematic and Evolutionary Microbiology, 2010, vol. 60, pp. 1721-1724, Published and available online on Sep. 4, 2009.*
Jin et al, Biol Pharm Bull, vol. 31, #8, pp. 1621-1625, 2008.*
Akaza, H., "Prostate Cancer Prevention and Enterobacteria," Probiotics and Cancer Prevention, vol. 1, pp. 2-7, (2008) (with partial English translation).
Tsuji, H., et al., "Isolation and identification of equol-producing bacterium from human feces," Japan Society for Bioscience, Biotechnology, and Agrochemistry, p. 123, 2P0981A, (Mar. 5, 2009) (with English Abstract).
Lampe, J.W., et al., "Urinary Equol Excretion with a Soy Challenge: Influence of Habitual Diet," Proc. Soc. Exp. Biol. Med., vol. 217, pp. 335-339, (1998).
Wang, X.-L., et al., "Enantioselective Synthesis of S-Equol from Dihydrodaidzein by a Newly Isolated Anaerobic Human Intestinal Bacterium," Applied and Environmental Microbiology, vol. 71, No. 1, pp. 214-219, (Jan. 2005).
Minamida, K., et al., "Production of Equol from Daidzein by Gram-Positive Rod-Shaped Bacterium Isolated from Rat Intestine," Journal of Bioscience and Bioengineering, vol. 102, No. 3, pp. 247-250, (2006).
International Search Report and English translation of Written Opinion issued May 18, 2010 in PCT/JP10/001272 filed Feb. 25, 2010.

* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

The present invention is directed to a microorganism having an ability of converting daidzein to equol in 24 hours of 50% or higher; a food/beverage or pharmaceutical composition containing the microorganism; an equol production method employing the microorganism; and a nucleic acid fragment which can specifically detect the microorganism.

6 Claims, 2 Drawing Sheets

```
                         SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      PCR primer eq430-F

<400> SEQUENCE: 1
gggacgaagt cattcgtga                                                 19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      PCR primer eq665-R

<400> SEQUENCE: 2
gcatccgagg cttccagtt                                                 19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer 27f

<400> SEQUENCE: 3
agagtttgat cmtggctcag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer 1552r

<400> SEQUENCE: 4
aaggaggtga tccarccgca                                                20
```

EQUOL-PRODUCING BACTERIUM AND USE THEREOF

CROSS-REFERENCE TO RELATED APPLICATIONS

This application is a National Stage of PCT/JP10/001,272 filed Feb. 25, 2010 and claims the benefit of JP 2009-042867 filed Feb. 25, 2009.

TECHNICAL FIELD

The present invention relates to an equol-producing bacterium and to use thereof.

BACKGROUND ART

Isoflavones, which are contained at high levels in soy foods, are known to be functional components effective for mitigating menopausal syndrome such as indefinite complaint; preventing osteoporosis; preventing hyperlipidemia and arteriosclerosis; preventing breast cancer and prostate cancer; etc. Recent studies have revealed that daidzein, a kind of isoflavone, is metabolized by the mediation of enterobacteria in the body to equol, which has stronger estrogen-like action and anti-oxidant action. Thus, equol has attracted attention as one of the important active ingredients exhibiting the aforementioned effects in the body.

Meanwhile, production of equol from daidzein does not equally occur in all humans, and equol-producing ability varies among individual humans. About 30 to 50% humans have equol-producing ability (Non-Patent Document 1). Therefore, extensive studies have been carried out to search for enterobacteria having equol-producing ability. Hitherto, the following microorganisms have been reported to have equol-producing ability: *Bacteroides ovatus, Streptococcus intermedius, Streptococcus constellatus* (Patent Document 1), *Lactococcus garvieae* (Patent Document 2), *Slackia* spp. strain TM-30, *Bifidobacterium adolescentis* strain TM-1, *Bifidobacterium breve* JCM 1273 (Patent Document 3), *Proprionobacterium freudenreichii, Bifidobacterium lactis, Lactobacillus acidophilus, Lactococcus lactis, Enterococcus faecium, Lactobacillus casei, Lactobacillus salivarius* (Patent Document 4), SNU-Julong 732 (Non-Patent Document 2), and Gram-positive bacterium do03 (Non-Patent Document 3).

However, since all the above-reported microorganisms exhibit a low conversion ability from daidzein as a substrate to equol (hereinafter may be referred to as "daidzein-to-equol conversion ability" or simply as "conversion-to-equol ability"), these microorganisms have not been employed in production of equol in the human body or in industrial production of equol.

PRIOR ART DOCUMENT

Patent Documents

[Patent Document 1] WO 99/7392
[Patent Document 2] WO 2005/42
[Patent Document 3] JP-A-2006-204296
[Patent Document 4] JP-A-2006-504409

Non-Patent Documents

[Non-Patent Document 1] Proc. Soc. Exp. Biol. Med., Vol. 217, No. 3, p. 335-339 (1998)
[Non-Patent Document 2] Appl. Environ. Microbiol., Vol. 71, p. 214-219 (2005)
[Non-Patent Document 3] J. Biosci. Bioeng., Vol. 102, p. 247-250 (2006)

SUMMARY OF THE INVENTION

Problems to be Solved by the Invention

Thus, an object of the present invention is to provide a microorganism exhibiting high conversion efficiency to equol. Another object is to provide a food/beverage or pharmaceutical composition containing the microorganism. Still another object is to provide a method for producing equol by use of the microorganism. Yet another object is to provide a nucleic acid fragment which can specifically detect the microorganism.

Means for Solving the Problems

The present inventors have carried out extensive studies in order to attain the aforementioned objects, and have found that a microorganism exhibiting high conversion efficiency to equol can be found through sub-culturing feces of a human who has equol-producing ability in a selection culture medium for the target microorganism having conversion-to-equol ability, which medium was previously developed by some of the present inventors. The present invention has been accomplished on the basis of this finding.

Accordingly, the present invention provides a microorganism which has an ability of converting daidzein to equol in 24 hours at a rate of 500 or higher.

The present invention also provides a food/beverage or pharmaceutical composition comprising the aforementioned microorganism having a conversion-to-equol ability.

The present invention also provides a method for producing equol, comprising causing, to act on daidzein, the aforementioned microorganism having a conversion-to-equol ability.

The present invention also provides a nucleic acid fragment which can specifically detect the aforementioned microorganism having a conversion-to-equol ability.

Effects of the Invention

The microorganism of the present invention, which exhibits very high conversion efficiency to equol, can be applied to food/beverage products and pharmaceuticals which aim at production of equol in the human body, and can be used for the purpose of treatment, amelioration, prevention, etc. of a variety of equol-effective diseases and disorders such as menopausal syndrome such as indefinite complaint; osteoporosis; hyperlipidemia; arteriosclerosis; breast cancer; prostate cancer; and premenstrual syndrome. When the present invention is applied to industrial production of equol, equol can be recovered at high concentration. Thus, post-operation such as separation/purification can be facilitated, leading to remarkably efficient production of equol. By use of the nucleic acid fragment of the present invention, a microorganism having a conversion-to-equol ability can be detected in feces and the digestive tract contents. When the microorganism having a conversion-to-equol ability is quantitated by use of the nucleic acid fragment, an equol-producing ability intrinsic to individuals can be readily investigated.

MODES FOR CARRYING OUT THE INVENTION

In the present invention, the "conversion-to-equol ability" may be determined by adding daidzein (substrate of equol) to a culture medium at a final concentration of 100 µM; inoculating a target microorganism into the medium at a concentration of $10^7$ cells/mL-medium; maintaining the medium at 37° C. for a specific period of time; determining the equol concentration of the medium; comparing the equol concentration to the initial daidzein concentration; and inputting the data to the following formula.

Conversion-to-equol ability(%)=(equol concentration of the culture containing the target microorganism)/(initial daidzein concentration of the culture)×100

The culture is preferably performed under anaerobic conditions in order to reproduce the conditions of the human enteric canal. The culture medium is preferably a GAM medium.

The equol concentration may be determined through a routine technique such as liquid chromatography or LC-MS.

In the present invention, the "microorganism which has an ability of converting daidzein to equol in 24 hours at a rate of 50% or higher" refers to a microorganism which exhibits a conversion-to-equol ability of 50% or higher after maintaining at a specific temperature for 24 hours. Preferably employed is a microorganism which exhibits a conversion-to-equol ability of 80% or higher after maintaining at a specific temperature for 24 hours, more preferably 100%. Alternatively, a microorganism which exhibits a conversion-to-equol ability of 50% or higher after maintaining for a shorter period of time; e.g., 8 hours, at a specific temperature is also preferably employed. An example of such a microorganism is a bacterium belonging to the genus *Slackia*.

In a more specific procedure, the microorganism of the present invention having a conversion-to-equol ability may be selected through screening. Specifically, a specimen (e.g., feces) possibly containing a microorganism having a conversion-to-equol ability is sub-cultured in a selective medium for a microorganism having a conversion-to-equol ability, which medium was previously developed by some of the present inventors (WO 2007/52740), while the ability of conversion of daidzein to equol is monitored. Examples of preferred specimens possibly containing a microorganism having a conversion-to-equol ability include feces and digestive tract contents of a human subject having an equol-producing ability (equol-producer). A feces specimen to be employed is preferably centrifugally washed in advance.

One of the bacteria having a conversion-to-equol ability and belonging to the genus *Slackia* which was obtained through the aforementioned procedure was deposited as *Slackia* sp. YIT 11861 (FERM BP-11231) in the National Institute of Advanced Industrial Science and Technology, International Patent Organism Depositary (Central 6th, 1-1-1 Higashi, Tsukuba City, Ibaraki, 305-8566, Japan) on Feb. 3, 2009. The phylogenetic systematics and biochemical properties of *Slackia* sp. YIT 11861 will next be described.

The 16S rRNA nucleotide sequence of $\geq 1400$ bp of *Slackia* sp. YIT 11861 was determined through a routine method, and homology search was performed in a public DNA database (DDBJ) by means of the FASTA program. As a result, this bacterium strain was found to have a 16S rRNA homology of 92.4% with respect to a known bacterium strain *Slackia exigua* ATCC $700122^T$ (accession No.: AF101240) belonging to the genus *Slackia*. The nucleotide sequence of another bacterium obtained from the DNA data base was subjected to multiple alignments, and the bacterium strain of the invention was analyzed in terms of molecular phylogeny through the NJ method. As a result, the strain was found to belong to the family Coriobacteriaceae, the genus *Slackia*. The strain was found to have a homology of 99% or higher with respect to *Slackia* spp. TM-30 disclosed in Patent Document 3 and with respect to three human-derived uncultured bacteria (accession Nos.: EF071271, DQ797152, and AY916234). These bacterium strains formed a cluster.

The biochemical properties of the bacterium strain of the present invention was found to differ from *S. exigua* ATCC $700122^T$ in that the strain was positive to alkaline phosphatase, and negative to arginine arylamidase, proline arylamidase, phenylalanine arylamidase, leucine arylamidase, tyrosine arylamidase, alanine arylamidase, glycine arylamidase, histidine arylamidase, and serine arylamidase; and to differ from *Slackia* spp. TM-30 in that the strain utilized D-mannose and D-raffinose and was positive to alkaline phosphatase. Thus, the strain *Slackia* sp. YIT 11861 was found to differ from the known strains.

The food/beverage or pharmaceutical composition of the present invention containing a microorganism having a conversion-to-equol ability may be employed as an equol-level-enhancer in the body, blood, intestine (e.g., large intestine), etc., and employed for the purpose of treatment, amelioration, prevention, etc. of a variety of isoflavone-effective diseases and disorders such as menopausal syndrome such as indefinite complaint; osteoporosis; hyperlipidemia; arteriosclerosis; breast cancer; prostate cancer; and premenstrual syndrome. Particularly when the composition is applied to a human subject having no equol-producing ability (non-equol-producer) or a human subject having low equol-producing ability, a variety of isoflavone-effective diseases and disorders can be prevented in everyday life. In addition, the composition is preferably applied to human subjects of middle to old age, who have higher risk for menopausal syndrome such as indefinite complaint, osteoporosis, and cancer.

No particular limitation is imposed on the mode of use of the microorganism of the present invention having a conversion-to-equol ability, and either viable cells or thermally denatured cells (killed cells) may be used. Also, a lyophilized product thereof, a culture product (e.g., culture supernatant), a treated cell product, etc. may be used. Notably, since the conversion-to-equol ability is considered to be exerted by an enzyme originating from the microorganism, the microorganism is preferably employed in a state that inactivation of the enzyme is inhibited.

The composition of the present invention may further contain adonitol, arabinose, erythritol, galactose, lactitol, melezitose, trehalose, ribose, sorbose, xylose, inositol, or sorbitol. These saccharides can selectively maintain or proliferate the microorganism having a conversion-to-equol ability or can enhance the conversion-to-equol ability of the microorganism, to thereby elevate the equol level. Therefore, when such a saccharide is used in combination with the microorganism of the present invention having a conversion-to-equol ability, the mixture can serve as a more potent equol-level-enhancer.

These saccharides may be used singly or in combination of two or more species. Either D-form or L-form thereof may be used, but the D-form is preferably used. An anhydrate or a hydrate such as a pentahydrate may also be used.

Trehalose has the isomers of α,α-form, α,β-form, and β,β-form which differ in the bonding fashion between two glucose molecules. Among them, any isomer form may be used, but the α,α-form is preferred. Inositol includes nine stereoisomers: myo-inositol, D(+)-inositol, L-(−)inositol, muco-inositol, scyllo-inositol, cis-inositol, epi-inositol, allo-inositol, and neo-inositol. In nature, myo-inositol, D(+)-inositol, L-(−)inositol, muco-inositol, and scyllo-inositol are present. From the viewpoint of availability, myo-inositol is preferably used. Needless to say, two or more stereoisomers of inositol may be used in combination.

The saccharide employed in the present invention may be a commercial product such as a synthetic product or a natural extract. Alternatively, a natural material containing a large amount of the saccharide may also be used. Specific examples of the material containing a large amount of adonitol include plant root and a material containing riboflavine. Specific examples of the material containing a large amount of sorbose include fruits. Specific examples of the material containing a large amount of melezitose include nectar and a plant secretion. Specific examples of the material containing a large amount of trehalose include fungi.

The composition of the present invention may further contain daidzein. Since daidzein serves as a substrate to form equol, use of daidzein in combination with the microorganism of the present invention having a conversion-to-equol ability and with the aforementioned saccharides provides a more potent equol-level-enhancer. Daidzein used in the present invention may be a commercial product such as a synthetic product or a natural extract. Alternatively, a natural material containing a large amount of daidzein or a processed product thereof may also be used. Specific examples of the material containing a large amount of daidzein include soybean, common peas, kuzu (*Pueraria hirsuta*), and clover. Examples of the processed product include soybean curd (tofu), soy milk, fried bean curd (abura-age), fermented soybeans (natto), soy sauce (shoyu), soybean paste (miso), and tempeh. Since an isoflavone glycoside is transformed into a corresponding aglycon by the action of enterobacteria present in the body, daidzein may be employed as a glycoside form such as daidzin, malonyldaidzin, or acetyldaidzin. Alternatively, an intermediate metabolite of conversion of daidzein to equol, for example, dihydrodaidzein may also be used. As used herein, the term "daidzein" also refers to these glycoside forms and intermediate metabolites.

No strict limitation is imposed on the dose of the food/beverage or pharmaceutical composition of the present invention containing a microorganism having a conversion-to-equol ability. Preferably, the dose is predetermined for attaining the target effect in accordance with different modes of use; e.g., the target subjects and the target diseases and disorders. The daily microorganism dose (as reduced to viable cells) is preferably $10^5$ cells to $10^{10}$ cells, particularly preferably $10^6$ cells to $10^9$ cells. The saccharide content of the composition is preferably 0.5 to 50 mass %, more preferably 1 to 10 mass %, and the daidzein content of the composition (as reduced to daidzein) is preferably 5 to 2,000 μM, more preferably 100 to 800 μM.

The composition of the present invention may be administered orally or parenterally. However, oral administration of the composition is preferred. In one mode of administration, the composition containing as an active ingredient a microorganism having a conversion-to-equol ability is mixed with a solid or liquid nontoxic pharmaceutical carrier selected depending on the administration method (e.g., oral administration, rectal administration, or injection), to thereby produce a common pharmaceutical preparation.

Examples of the aforementioned pharmaceutical preparation include solid preparations such as tablet, granules, powder, and capsule; liquid preparations such as solution, suspension, and emulsion; and lyophilized preparations. These preparations may be produced through a common manufacturing method. Examples of the nontoxic pharmaceutical carrier include starch, dextrin, fatty acid glyceride, polyethylene glycol, hydroxyethyl starch, ethylene glycol, polyoxyethylene sorbitan fatty acid ester, amino acid, gelatin, albumin, water, and physiological saline. If required, the preparation may appropriately contain common additives such as a stabilizer, a wetting agent, an emulsifier, a binder, a tonicity agent, and an excipient.

The food/beverage composition of the present invention may be used as it is or together with a variety of nutritional components. The food/beverage composition of the present invention may be used as a health food or food material for the purpose of elevating the in-vivo equol level, or useful for amelioration, prevention, etc. of menopausal syndrome such as indefinite complaint; osteoporosis; hyperlipidemia; arteriosclerosis; breast cancer; prostate cancer; and premenstrual syndrome. These foods and beverages, or their containers, may have a label indicating such effects. Specifically, when employed as a food or beverage, the composition of the present invention is appropriately mixed with an additive which can be used in a food or beverage, and the mixture may be prepared, through conventional means, into a form suitable for eating and drinking; for example, granules, particles, tablet, capsule, or paste. The composition may be added to a variety of foods; for example, processed meat products (e.g., ham and sausage), processed fish products (e.g., kamaboko and chikuwa), bread, confectionary, butter, powdered milk, and fermented milk product, or may be added to beverages such as water, fruit juice, milk, soft drink, and tea-based beverage. As used herein, the term "food or beverage" encompasses animal feeds.

Through causing the microorganism of the present invention having a conversion-to-equol ability to act on daidzein, equol can be produced at high efficiency. No particular limitation is imposed on the form of the microorganism having a conversion-to-equol ability, and either viable cells or thermally denatured cells (killed cells) may be used. Also, a lyophilized product thereof, a culture product (e.g., culture supernatant), a treated cell product, etc. may be used. Notably, since the conversion-to-equol ability is considered to be exerted by an enzyme originating from the microorganism, the microorganism is preferably employed in a state that inactivation of the enzyme is inhibited. As compared with known equol-producing bacteria, the microorganism of the present invention has remarkably high conversion-to-equol ability and thus can produce equol at high yield and low cost.

In a specific production procedure, daidzein is added to a culture medium at a concentration of 10 to 1,000 μM, and the microorganism of the present invention having a conversion-to-equol ability is inoculated into the medium at a concentration of $10^6$ to $10^{10}$ cells/mL-medium, followed by anaerobic culture at 37° C. for 8 hours or longer, to thereby produce equol. To the culture medium, at least one saccharide having an equol-level-enhancement action selected from among adonitol, arabinose, erythritol, galactose, lactitol, melezitose, trehalose, ribose, sorbose, xylose, inositol, and sorbitol is preferably added in an amount of 1 to 10 mass %. Other appropriate components such as nitrogen source may also be added to the medium. However, use of a component which inhibits proliferation of the microorganism of the present invention having a conversion-to-equol ability or which inhibits the conversion-to-equol ability is not preferred. Examples of the component which can be added to the medium include peptone, trypticase peptone, yeast extract, hemin, vitamin such as vitamin K1, L-cysteine hydrochloride, $KH_2PO_4$, $K_2HPO_4$, NaCl, $(NH_4)_2SO_4$, $CaCl_2$, and $MgSO_4$. Except daidzein and the saccharide having an equol-level-enhancement action, the culture medium of the present invention may have a composition of, for example, the PY medium, the GAM medium, the BHI medium, etc.

Daidzein, serving as a substrate, may be a commercial product such as a synthetic product or a natural extract. Alternatively, a natural material containing a large amount of daidzein or a processed product thereof may also be used. Still alternatively, daidzein may be employed as a glycoside form such as daidzin, malonyldaidzin, or acetyldaidzin. In this case, a known microorganism (e.g., *Bifidobacterium*) or enzyme (e.g., β-glucosidase) which can transform an isoflavone glycoside into a corresponding aglycon may be used in combination with the microorganism of the present invention.

Instead of performing culturing with the microorganism of the present invention having a conversion-to-equol ability, an enzyme originating from the microorganism and having a conversion-to-equol ability may be used. No particular limitation is imposed on the mode of use of the enzyme, and specific examples of the mode include use of a culture product as is; use of a concentrate or pellets of a culture product obtained through a concentration process such as centrifugation or membrane treatment; use of resting cells; use of dry cells; use of broken cells; use of crude enzyme solution; use of purified enzyme solution; and use of enzyme powder.

No particular limitation is imposed on the purification conditions and purification degree of the enzyme, and a conventional purification technique may be employed. In one purification procedure, a microorganism having a conversion-to-equol ability is cultured, and cells are separated from the culture product by separation means such as centrifugation, organic membrane separation, or inorganic membrane separation. When the culture supernatant contains the target enzyme, the recovered supernatant may be employed as a crude enzyme solution. In the case where the cells contain the target enzyme, the cells are physically broken by means of a homogenizer or through ultrasonication. Alternatively, the cells are enzymatically treated with a cell wall lysis enzyme, to thereby provide an endo-extract, which may be employed as a crude enzyme solution. These crude enzyme solutions may be treated through, for example, salting out with ammonium sulfate, dialysis, gel filtration chromatography, ion-exchange chromatography, adsorption chromatography, and affinity chromatography, in appropriate combination, to thereby provide a high-purity enzyme solution having higher purification degree.

The microorganism having a conversion-to-equol ability or the enzyme originating from the microorganism having a conversion-to-equol ability may be an immobilized product obtained through a conventional immobilization technique. No particular limitation is imposed on the immobilization technique, and examples of the immobilization technique include carrier-bonding, cross-linking, and entrapment. Examples of carrier-bonding include covalent bonding, ionic bonding, and physical adsorption; examples of cross-linking include the glutaraldehyde method; and examples of entrapment include lattice-form entrapment and microcapsule-entrapment. More specific examples include adsorption onto activated carbon, sawdust, etc.; bonding to CM-cellulose, P-cellulose, DEAE cellulose, ECTEOLA-cellulose, etc.; cross-linking with glutaraldehyde, tolylene diisocyanate, etc.; and entrapment with acrylamide, κ-carrageenan, alginic acid, gelatin, cellulose acetate, etc. The thus-immobilized bacterium or enzyme may be employed in a conventional method (e.g., batch-mode, with column, etc.) and singly, repeatedly, or continuously.

In the above equol production, an equol-containing culture product (e.g., culture supernatant) as is may be employed. Alternatively, the culture product may be subjected to a conventional separation/purification process such as column chromatography or extraction with organic solvent, to thereby separate equol from the culture product. The thus-obtained culture product may be adsorbed onto an ion-exchange column, followed by elution with methanol, to thereby yield an equol purified product.

The nucleic acid fragment which can specifically hybridize with the DNA and/or RNA of the microorganism of the present invention having a conversion-to-equol ability was obtained by comparing, with a database (DDBJ, Genbank, etc.), the nucleotide sequence of *Slackia* sp. YIT 11861 which the present inventors previously obtained through sequencing. In the production of the nucleic acid fragment of the present invention, a 16S rRNA gene, which is highly reliable for serving as a phylogenic index, was employed as a target. Since the analysis of the fragment requires PCR or similar means, a DNA was employed instead of an RNA.

In designing of the nucleic acid fragment, the nucleotide sequence of the 16S rRNA gene of a target bacterium belonging to the genus *Slackia* having a conversion-to-equol ability was aligned with that of a closely related bacterium. Specifically, the alignment was conducted by selecting a closely related bacterium belonging to the family Coriobacteriaceae (the genus *Atopobium, Collinsella*, etc.) on the basis of the phylogenic system employing the current gene sequence as an index. As a result, nucleic acid fragments having a nucleotide sequence of SEQ ID NO: 1 or 2 were obtained. The nucleic acid fragment which can specifically hybridize with the DNA and/or RNA of the target bacterium is not limited to the thus-designed sequence, and those skilled in the art can conceive other equivalents on the basis of common technical sense. Examples of such equivalents include a nucleic acid fragment having a nucleotide sequence complementary to the thus-designed sequence, and a nucleic acid fragment which has a nucleotide sequence homologous to any of the above sequences and which is functionally equivalent to the above nucleic acid fragment. Examples of the nucleic acid fragment which has a homologous nucleotide sequence and which is functionally equivalent include the following nucleic acid fragments (a) to (c):

(a) a nucleic acid fragment which has a nucleotide sequence represented by the nucleotide sequence of SEQ ID NO: 1 or 2 or a nucleotide sequence complementary thereto, wherein one to several bases, preferably 1 to 10 bases, are deleted, substituted, or added;

(b) a nucleic acid fragment which has a nucleotide sequence having an identity of 90% or higher, preferably 95% or higher, more preferably 99% or higher, to the nucleotide sequence of SEQ ID NO: 1 or 2 or a nucleotide sequence complementary thereto; and (c) a nucleic acid fragment which hybridizes under stringent conditions with a DNA fragment having the nucleotide sequence of SEQ ID NO: 1 or 2 or a nucleotide sequence complementary thereto, so long as these examples can be employed in detection, identification, and quantitation of the target microorganism.

The identity of a nucleotide sequence is calculated by means of a homology analysis program, GENETYX(R). The term "stringent conditions" refers to, for example, the case where hybridization is carried out in a solution containing 50% formamide, 5×SSC, 5×Denhardt's solution, and 250 mg/mL sermon sperm DNA at 42° C. for 16 to 24 hours.

The thus designed nucleic acid fragments may be synthesized artificially, according to the nucleotide sequences thereof, by means of a DNA synthesizer. The specificity of the nucleic acid fragments was investigated by use of each nucleic acid fragment as a primer and confirmed by use of, as indices, the presence of amplicons with respect to the following 18 closely related strains *Atopobium fosser* JCM 9981$^T$, *Atopobium minutum* JCM 1118$^T$, *Atopobium parvulum* JCM 10300$^T$, *Atopobium rimae* JCM 10299$^T$, *Atopobium vaginae* DSM 15829$^T$, *Collinsella aerofaciens* ATCC 25986$^T$, *Collinsella intestinalis* JCM 10643$^T$, *Collinsella stercorin* JCM 10641$^T$, *Cryptobacterium curtum* DSM 15641$^T$, *Denitrobacterium detoxificans* CCUG 47027$^T$, *Eggerthella hongkongensis* JCM 14552$^T$, *Eggerthella lenta* ATCC 25559$^T$, *Eggerthella sinensis* JCM 14551$^T$, *Olsenella profusa* JCM 14553$^T$, *Olsenella uli* JCM 12494$^T$, *Slackia exigua* JCM 11022$^T$, *Slackia faecicanis* JCM 14555$^T$, and *Slackia heliotriniereducens* JCM 14554$^T$, and the presence of amplicons with respect to 27 typical enterobacteria and pathogenic bacteria strains (shown in the Examples below). As a result, suitable specificity was realized.

Since the nucleic acid fragment of the present invention has specificity to a microorganism having a conversion-to-equol ability, the microorganism having a conversion-to-equol ability can be specifically detected, identified, and quantitated through PCR with the DNA or RNA recovered from human or animal feces or digestive tract contents, or through FISH (fluorescence in situ hybridization) or similar means. Through quantitation of the microorganism having a conversion-to-equol ability, the equol-producing ability which an individual originally possesses can be readily checked, whereby the risk of suffering a variety of equol-effective diseases and disorders such as menopausal syndrome such as indefinite complaint; osteoporosis; hyperlipidemia; arteriosclerosis; breast cancer; prostate cancer; and premenstrual syndrome can be determined. Thus, precautionary measures (e.g., administration of the composition of the present invention) can be effectively taken to a human having no or low equol-producing ability. In addition, through, for example, administration of the composition of the present invention, a human who suffers from such a disease and who has no or low equol-producing ability can be treated or ameliorated.

PCR or RT-PCR analysis may be performed through, for example, the following steps: (1) a step of extracting a DNA or RNA contained in a specimen; (2) a step of performing PCR or RT-PCR by use of one or more of the aforementioned nucleic acid fragments; and (3) a step of detecting a DNA fragment amplified in step (2). When amplification reaction is performed by using the nucleic acid fragment of the present invention in combination with a template DNA derived from the specimen (cDNA in the case where the template is RNA), a DNA fragment (PCR product) specific to a target bacterium belonging to the genus *Slackia* can be obtained. Through electrophoresis of the thus-obtained DNA fragment, the target bacterium belonging to the genus *Slackia* can be specifically detected and identified based on the presence or absence of a band.

When PCR is performed with stepwise dilution of the template DNA or RNA (cDNA), a bacterium belonging to the genus *Slackia* can be quantitated. In quantitation by PCR, the aforementioned method may be employed, but real-time PCR is more preferably employed. Through monitoring the PCR product formed through PCR amplification and determining the number of PCR cycles at the time when the DNA level has reached a certain amount, a bacterium belonging to the genus *Slackia* contained in the specimen can be quantitated.

Monitoring of the PCR product formed through amplification may be performed by labeling the PCR product with an intercalator fluorescent dye such as SYBR(R) Green I and measuring the fluorescence intensity at each PCR stage. Since the intercalator dye enhances fluorescence intensity via intercalation with a double-strand nucleic acid, the PCR product formed through PCR of the DNA (cDNA in the case where the template is RNA) of the target bacterium can be correctly assayed. Among intercalator dyes, SYBR(R) Green I is particularly preferably employed.

Through determination of the number of PCR cycles at the time when the fluorescence intensity (DNA level) has reached a predetermined level (hereinafter referred to as $C_T$ value), the target bacterium contained in the specimen can be quantitated, detected, or identified. This analysis may also be accomplished by use of TaqMan probe, Molecular Beacon, labeled with a fluorescent dye, etc. A TaqMan probe or Molecular Beacon is a probe in which a fluorescent dye and a quencher are bonded to an oligonucleotide having a homology to an internal sequence of a region which is amplified through PCR. The probe is additionally employed in PCR. Since fluorescence depending on the PCR amplification reaction is emitted through interaction between the fluorescent dye and the quencher bonded to the probe, the PCR product formed through amplification can be monitored by measuring the fluorescence intensity at each PCR stage.

The target bacterium belonging to the genus *Slackia* contained in the specimen can be quantitated, detected, or identified by means of a calibration curve between $C_T$ value and logarithmic cell count determined by the culturing method or a similar method. Specifically, $C_T$ values are plotted along the vertical axis, and logarithmic target cell counts are plotted along the horizontal axis, to thereby draw a calibration curve in advance. Then, a $C_T$ value obtained through PCR is applied to the calibration curve, whereby the target bacterium belonging to the genus *Slackia* contained in the specimen can be quantitated, detected, or identified.

The nucleic acid fragment of the present invention is employed as a primer in PCR, and the fragment as is may also be employed as a probe and employed with a known universal primer, oligonucleotide, etc., in combination.

Examples of the analysis employing the nucleic acid fragment of the present invention as a probe include in situ hybridization and dot blot hybridization. Of these, in situ hybridization is preferred as a rapid analytical method, since it requires no step of extracting nucleic acid contained in a specimen. More preferably, FISH, employing a nucleic acid fragment labeled with a fluorescent dye, is employed.

Specifically, FISH may be performed through the following steps: (1) a step of fixing a specimen with formaldehyde or formalin; (2) a step of applying the fixed specimen onto a glass slide or membrane filter; (3) a step of performing hybridization with a nucleic acid fragment labeled with the fluorescent dye; (4) a step of washing out the nucleic acid fragment remaining after hybridization and non-specifically bound nucleic acid fragments; and (5) a step of visually observing the hybridization results under a fluorescence microscope or taking an image thereof by means of a CCD camera or a similar apparatus.

When the target bacterium belonging to the genus *Slackia* is present in the specimen, the bacterium hybridizes with the employed nucleic acid fragment, and the positive signal is obtained after hybridization. On the basis of the positive signal, the bacterium can be specifically detected or identified. Through counting the bacterium cells, the bacterium can be quantitated.

The present invention will next be described in more detail by way of Test Examples and Examples, which should not be construed as limiting the invention thereto.

EXAMPLES

Test Example 1

Recovery of Bacterium Having a Conversion-to-Equol Ability

Fresh feces excreted by a healthy equol producer was sufficiently suspended in 10-times volume of a diluent (0.00255% of $KH_2PO_4$, 0.00255% of $K_2HPO_4$, 0.006% of NaCl, 0.00255% of $(NH_4)_2SO_4$, 0.000255% of $CaCl_2$, 0.000255% of $MgSO_4$, 0.1% of a 0.1% resazurin solution, 2.2% of a 8% $Na_2CO_3$ solution, and 0.05% of L-cysteine hydrochloride) in the presence of glass beads ($\phi$: 3 mm) in anaerobic conditions, and the residue of the suspension was removed through sterilized gauze. The thus-purified suspension was centrifuged at 8,000×g for 10 minutes, and the precipitate was suspended in an equivolume diluent, and the resultant was maintained at −30° C. under freezing conditions. The frozen feces diluted solution was thawed upon use and centrifuged at 8,000×g for 10 minutes. The thus-recovered precipitate was suspended in a PY medium containing sorbose as a sugar source (0.5% of peptone, 0.5% of trypticase peptone, 1% of yeast extract, 0.00005% of hemin, 0.0001% of vitamin K1, 0.05% of L-cysteine hydrochloride, 0.0006% of $KH_2PO_4$, 0.0006% of $K_2HPO_4$, 0.0012% of NaCl, 0.0006% of $(NH_4)_2SO_4$, 0.00006% of $CaCl_2$, and 0.00006% of $MgSO_4$). The suspension was incubated at 37° C. under a gas mixture ($N_2:H_2:CO_2=88:7:5$) for 24 to 48 hours. The culturing was repeated six times (to the 7th generation). The resultant culture product was diluted with the same medium to prepare a $10^6$-fold diluted solution, and an aliquot (50 μL) of the solution was applied to 20 sheets of GAM (1% glucose-added) agar plate medium. The plates were incubated at 37° C. for 72 hours in an anaerobic glove box, to thereby form colonies. The thus-obtained colonies were classified into 26 types in terms of colony characteristics (surface appearance, size) and Gram-stained images. A typical colony of each type was selected, and the cell samples from the colony was inoculated to a GAM (1% glucose-added) liquid medium containing daidzein at a final concentration of 100 μM, followed by incubation at 37° C. for 24 hours under a gas mixture ($N_2:H_2:CO_2=88:7:5$). The equol concentration of each of the thus-obtained culture solutions was determined through HPLC, to thereby detect a Gram-positive *bacillus* having high daidzein-to-equol conversion ability. HPLC was performed under the following conditions.

Apparatus: LC module 1 (Waters)
Column: YMC-Pack CN (product of Y.M.C)
Detection: UV spectrophotometer (measurement wavelength: 280 nm)
Column temperature: 40° C.
Mobile phase: 0.1% formic acid solution/acetonitrile/methanol (87:3:10) mixture
Flow rate: 2.5 mL/min
Sample injection: 10 μL

Test Example 2

Figure 1:
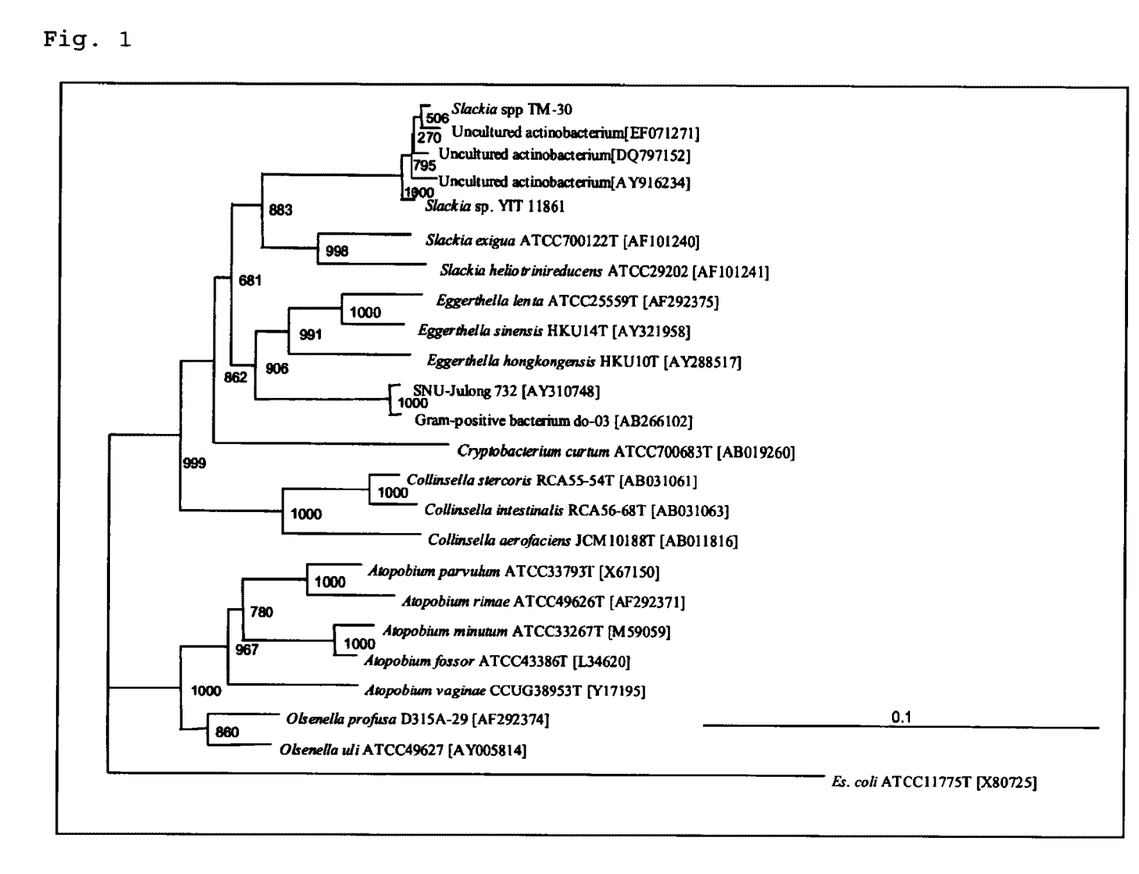
FIG. 1: A chart showing the molecular phylogenetic tree of *Slackia* sp. YIT 11861 (code in [ ] represents an accession number, and the numerical values represent Boot strap values).

Molecular Phylogenetic Analysis and Biochemical Properties of Bacterium Having a Conversion-to-Equol Ability PCR was performed, targeted with 16S ribosomal RNA (16S rRNA), by use of a genome of the bacterium isolated in Test Example 1 as a template and primers 27f (SEQ ID NO: 3) and 1552r (SEQ ID NO: 4), to thereby yield an amplification product of about 1,500 bp. The thus-obtained fragment was employed as a template, and sequencing PCR was performed. The sequencing PCR was performed by means of BigDye(R) Terminator v3.1 Cycle Sequencing Kit (Applied Biosystems) according to a method disclosed in a product manual attached thereto. AB 3130 Genetic Analyzer (Applied Biosystems) was employed as a sequencer. Molecular phylogenetic analysis and homology analysis of 16S rRNA sequence were carried out by means of Clustal X v1.83, TreeView v1.6.6, and GENETIX(R) Ver. 7 (Genetics). As a result, the strain was found to belong to the family Coriobacteriaceae (FIG. 1). Although *Slackia exigua* ATCC $700122^T$ was the closest known phylogenetic relative, the strain exhibited a low homology (92.4%). The strain obtained in Test Example 1 was found to have a homology of 99% or higher with respect to *Slackia* spp. TM-30 disclosed in Patent Document 3 and these strains formed a cluster with uncultured bacterium strains registered in the database. Therefore, the strain of Test Example 1 was conceivably thought to be the same species as *Slackia* spp. TM-30.

The biochemical properties of the strain of Test Example 1 and *S. exigua* ATCC $700122^T$, which is the closest known phylogenetic relative analyzed through 16S rRNA sequence analysis, were investigated by means of Rapid ID 32A (SYSMEX bioMerieux Co., Ltd.). Each tested bacterium was cultured in a GAM (1% glucose-added) agar medium at 37° C. for 24 hours under anaerobic conditions. Two sheets of GAM (1% glucose-added) agar medium were employed with respect to one identification kit. Preparation of the bacterium solution applied to the kit, reaction, and determination were performed according to a manual attached to the kit. Table 1 shows the results. In analysis by means of Rapid ID 32A, the bacterium having a conversion-to-equol ability exhibited properties considerably different from those of *S. exigua* ATCC $700122^T$. Also, in analysis by means of Rapid ID 32A, the bacterium having a conversion-to-equol ability exhibited D-mannose utilization and D-raffinose utilization and was positive to alkaline phosphatase. These biochemical properties differ from those of *Slackia* spp. TM-30 disclosed in Patent Document 3. Therefore, the strain of Test Example 1 was found to be different from disclosed strains. Thus, the studies in molecular biology and biochemistry have revealed that the strain is thought to be a novel strain belonging to the genus *Slackia*, and the present inventors have denominated the strain as a bacterium belonging to the genus *Slackia*, YIT 11861 (*Slackia* sp. YIT 11861).

TABLE 1

Comparison of Biochemical Properties Analyzed by Means of Rapid ID 32A

| | *Slackia* sp. YIT 11861 | *Slackia exigua* ATCC $700122^T$ | *Slackia* spp. TM-30* |
|---|---|---|---|
| Urease | − | − | − |
| Arginine dihydrase | + | + | + |
| α-Galactosidase | − | − | − |
| β-Galactosidase | − | − | − |
| β-Galactosidase-6-phospate | − | − | − |
| α-Glucosidase | − | − | − |
| β-Glucosidase | − | − | − |
| α-Arabinosidase | − | − | − |
| β-Glucuronidase | − | − | − |
| N-Acetyl-β-glucosaminidase | − | − | − |
| D-Mannose | + | + | − |
| D-Raffinose | + | + | − |
| Glutamate decarboxylase | + | + | + |
| α-Fucosidase | − | − | − |
| Nitrate reduction | − | − | − |
| Indole | − | − | − |

TABLE 1-continued

Comparison of Biochemical Properties
Analyzed by Means of Rapid ID 32A

| | Slackia sp. YIT 11861 | Slackia exigua ATCC 700122$^T$ | Slackia spp. TM-30* |
|---|---|---|---|
| Alkaline phosphatase | + | − | − |
| Arginine arylamidase | − | + | + |
| Proline arylamidase | − | + | − |
| Leucylglycine arylamidase | − | − | − |
| Phenylalanine arylamidase | − | + | − |
| Leucine arylamidase | − | + | − |
| Pyroglutamate arylamidase | − | − | − |
| Tyrosine arylamidase | − | + | − |
| Alanine arylamidase | − | + | − |
| Glycine arylamidase | − | + | − |
| Histidine arylamidase | − | + | − |

TABLE 1-continued

Comparison of Biochemical Properties
Analyzed by Means of Rapid ID 32A

| | Slackia sp. YIT 11861 | Slackia exigua ATCC 700122$^T$ | Slackia spp. TM-30* |
|---|---|---|---|
| Glutamylglutamate arylamidase | − | − | − |
| Serine arylamidase | − | + | − |

*Disclosed in Patent Document 3

Test Example 3

Daidzein-to-Equol Conversion Activity of *Slackia* sp. YIT 11861

Daidzein-to-equol conversion activity of *Slackia* sp. YIT 11861 was investigated. The bacterium was inoculated into a GAM medium containing daidzein at a concentration of 100 or 400 μM at the cell concentration of $10^7$ cells/mL-medium, and the medium was maintained at 37° C. The equol concentration of the culture solution was determined through HPLC at a plurality of times during the course of culturing, to thereby determine daidzein-to-equol conversion activity.

The results are shown in Table 2. Activities of some bacterium strains disclosed in patent specifications and papers were also investigated and compared with the activity of the bacterium of the present invention. As a result, *Slackia* sp. YIT 11861 converted 100 μM daidzein to equol in incubation for 8 hours at a percent conversion of 95% and for 24 hours 100%, and 400 μM daidzein to equol in incubation for 24 hours at a percent conversion of 94% and for 96 hours 100%. In contrast, a Gram-positive bacterium do-03 strain (Non-Patent Document 3) converted 193 μM daidzein to equol in incubation for 48 hours at a percent conversion of 33% (initial cell concentration: undisclosed, final cell concentration: $OD_{660}$=0.277; conceivably $10^6$ to $10^8$ cells/mL-medium), and TM-30 strain converted 391 μM daidzein to equol in incubation for 24 hours at a percent conversion of merely about 1% (initial cell concentration: undisclosed, final cell concentration: $10^9$ cells/mL-medium). In the case of *L. gariviae* 92-90 strain, 72 hours were required for 100% conversion of merely 42 μM daidzein to equol, and no conversion (0%) occurred in incubation for 24 hours (initial cell concentration: $10^7$ cells/mL-medium). Thus, *Slackia* sp. YIT 11861 was found to have a daidzein-to-equol conversion activity remarkably higher than that of known bacterium strains.

TABLE 2

Daidzein-to-Equol Conversion Activity of *Slackia* sp. YIT 11861 and Comparison with Known Strains

| | Condition of reaction | | | Concentration of isoflavone (μM) | | | Daidzein to equol conversion rate (%) | Reference |
|---|---|---|---|---|---|---|---|---|
| Strain | Temp. (° C.) | Time (h) | Initial daidzen conc. (μM) | Daidzein | Equol | DHD* | | |
| *Slackia* sp. YIT 11861 | 37 | 6 | 100 | 49.7 | 44.4 | 1.8 | 44 | This study |
| | 37 | 8 | 100 | 0.9 | 95 | 5.5 | 95 | |
| | 37 | 24 | 100 | 0.8 | 107 | 1.1 | 100 | |
| | 37 | 24 | 400 | 1.2 | 376 | 31.5 | 94 | |
| | 37 | 96 | 400 | 2.1 | 417 | 0.0 | 100 | |
| Gram positive bacterium do-03 | 37 | 48 | 193 | 62.3 | 64 | 45.3 | 33 | Non-Patent Document 3 |
| | 37 | 96 | 193 | ND** | 139 | ND | 72 | |
| *Slackia* spp. TM-30 | 37 | 24 | 391 | 269 | 4.2 | ND | 1 | Patent Document 3 |
| *Lactococcus gariviae* strain 92-90 | 37 | 24 | 42 | 42 | 0 | 0 | 0 | Patent Document 2 |
| | 37 | 96 | 42 | 0 | 42 | 0 | 100 | |

DHD*: dihydrodaidzein,
ND**: Not described

Test Example 4

Designing of Nucleic Acid Fragment Specific to *Slackia* sp. YIT 11861

Figure 2:
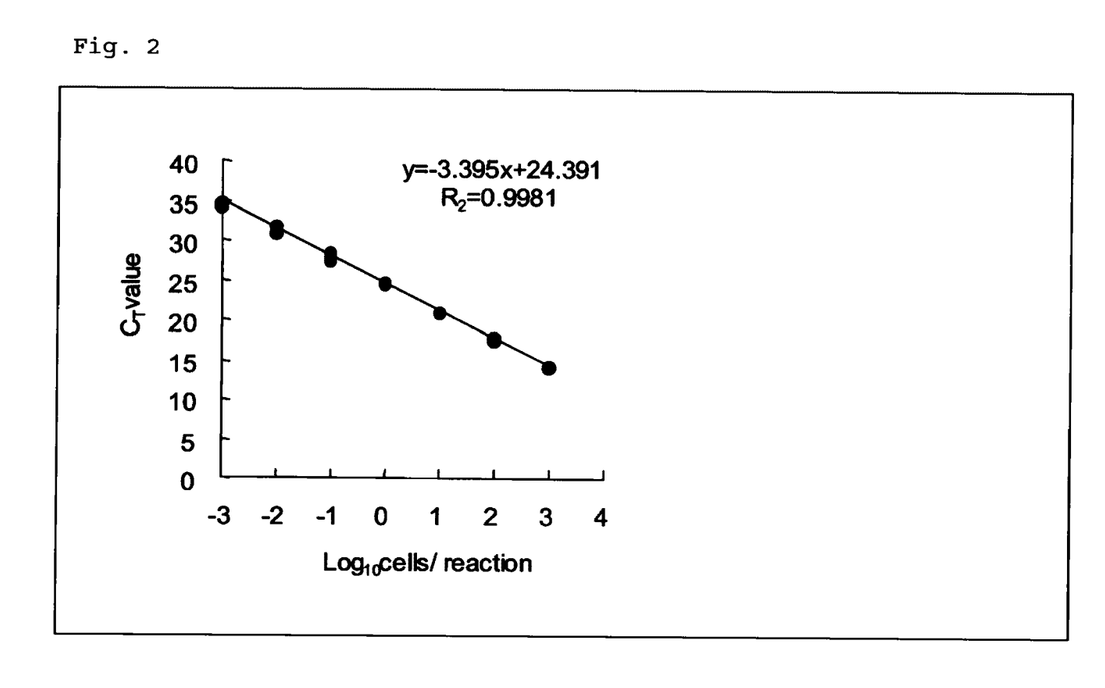
FIG. 2: A graph showing the detection sensitivity of the produced primer.

A primer was designed on the basis of a characteristic sequence of *Slackia* sp. YIT 11861. Specifically, a 16S rRNA sequence of a bacterium belong to the family Coriobacteriaceae was obtained from a public database (DDBJ/GENEBANK/EMBL), and the thus-obtained sequences of closely related strains were aligned with a rRNA sequence of the YIT 11861 strain by means of Clustal X v1.83, whereby primers eq430-F/eq665-R with respect to a specific region were designed (SEQ ID NOs: 1 and 2). The RNA extracted from *Slackia* sp. YIT 11861 cells ($2\times10^8$ cells/mL) was stepwise 10-fold-diluted so as to adjust the concentration (reduced to cell concentration) to $2\times10^6$ to $2\times10^{-1}$ cells/mL. An aliquot (5 μL) of the diluted RNA was employed as a template, and quantitative RT-PCR was performed. Quantitative RT-PCR was performed by means of OneStep RT-PCR kit (QIAGEN). The reaction mixture was subjected to reverse transcription at 50° C. for 30 minutes and then heated at 95° C. for 15 minutes in order to inactivate the reverse transcriptase. Subsequently, PCR was performed for 45 cycles (each cycle: 94° C. for 20 sec, 60° C. for 20 sec, and 72° C. for 50 sec). As a result, the PCR amplification by use of the primers was found to be correlated with the cell count in the range of $10^{-3}$ to $10^3$ cells. That is, $10^3$ cells per 1 g of feces can be quantitated (FIG. 2).

The specificity of the primers was studied with respect to typical enterobacteria, infection causal bacteria, and closely related strains belonging to the family Coriobacteriaceae, which are given in Table 3. Specifically, an RNA was extracted from the axenic culture of each strain whose cell count had been determined in advance through the DAPI staining method, and the RNA concentration (reduced to cell concentration) was adjusted to $2\times10^8$ cells/mL. RNA (equivalent to $1\times10^5$ cells/mL) was supplied in one reaction, and quantitative RT-PCR was performed under the aforementioned conditions. The reactivity of the aforementioned primer set with typical enterobacteria, infection causal bacteria, and closely related strains belonging to the family Coriobacteriaceae was investigated. Table 3 shows the results (+: CT≧40, −: CT<40).

The primer set was found to have high specificity only to *Slackia* sp. YIT 11861, and no cross-reaction was observed with respect to the other bacterium strains. In reaction involving nuclease-free water instead of an RNA sample, no amplification of non-specific products was observed.

TABLE 3

Tested Bacterium Strains and Specificity of Primer Set

| Taxon | Strain | Primer eq430F/eq665R |
|---|---|---|
| *Slackia* sp. YIT11861 | YIT 11861 | + |
| *Atopobium fosser* | JCM 9981 T | − |
| *Atopobium minutum* | JCM 1118 T | − |
| *Atopobium parvulum* | JCM 10300 T | − |
| *Atopobium rimae* | JCM 10299 T | − |
| *Atopobium vaginae* | DSM 15829 T | − |
| *Collinsella aerofaciens* | ATCC 25986 T | − |
| *Collinsella intestinalis* | JCM 10643 T | − |
| *Collinsella stercoris* | JCM 10641 T | − |
| *Cryptobacterium curtum* | DSM 15641 T | − |
| *Denitrobacterium detoxificans* | CCUG 47027 T | − |
| *Eggerthella hongkongensis* | JCM 14552 T | − |
| *Eggerthella lenta* | ATCC 25559 T | − |
| *Eggerthella sinensis* | JCM 14551 T | − |
| *Olsenella profusa* | JCM 14553 T | − |
| *Olsenella uli* | JCM 12494 T | − |
| *Slackia exigua* | JCM 11022 T | − |
| *Slackia faecicanis* | JCM 14555 T | − |
| *Slackia heliotrinireducens* | JCM 14554 T | − |
| *Bifidobacterium adolescentis* | ATCC 15703 T | − |
| *Bacteroides fragilis* | DSM 2151 T | − |
| *Clostridium perfringens* | JCM 1290 T | − |
| *Prevotella melaninogenica* | ATCC 25845 T | − |
| *Veillonella parvula* | ATCC 10790 T | − |
| *Lactobacillus acidophilus* | ATCC 4356 T | − |
| *Escherichia coli* | ATCC 11775 T | − |
| *Enterococcus faecalis* | ATCC 19433 T | − |
| *Staphylococcus aureus* | ATCC 12600 T | − |
| *Streptococcus mutans* | IFO 13955 T | − |
| *Campylobacter jejuni* | ATCC 33560 T | − |
| *Pseudomonus aeruginosa* | ATCC 10145 T | − |
| *Bifidobacterium longum* | ATCC 15707 T | − |
| *Bacteroides vulgatus* | JCM 5826 T | − |
| *Ruminococcus productus* | ATCC 27340 T | − |
| *Ruminococcus obeum* | ATCC 29174 T | − |
| *Clostridium orbiscindens* | DSM 6740 T | − |
| *Lactobacillus casei* | ATCC 334 T | − |
| *Citrobacter freundii* | ATCC 13316 T | − |
| *Enterobacter cloacae* | ATCC 13047 T | − |
| *Klebsiella pneumoniae* | ATCC 13883 T | − |
| *Enterococcus faecium* | ATCC 19434 T | − |
| *Staphylococcus epidermidis* | ATCC 14990 T | − |
| *Streptococcus salivarius* | ATCC 7073 T | − |
| *Acinetobacter calcoaceticus* | ATCC 14987 T | − |

TABLE 3-continued

Tested Bacterium Strains and Specificity of Primer Set

| Taxon | Strain | Primer eq430F/eq665R |
|---|---|---|
| *Bacillus cereus* | ATCC 12826 T | − |
| *Pseudomonas putida* | JCM 5963 T | − |

Test Example 5

Analysis of Human-Derived Samples

RNA was extracted from feces samples of 40 healthy volunteers. Each RNA sample was subjected to quantitative RT-PCR by use of the primers defined by SEQ ID NOs: 1 and 2. Specifically, feces (20 mg) was sampled from each volunteer, and immediately thereafter, total RNA was extracted through the AGPC method. The thus-obtained total RNA was appropriately diluted, and the diluted product was subjected to quantitative RT-PCR according to the method described in Test Example 4. The *Slackia* sp. YIT 11861 cell count of the sample was calculated from the reactivity of RNA extracted from *Slackia* sp. YIT 11861 cells whose count had been determined in advance. As a result, *Slackia* sp. YIT 11861 was detected in 16 volunteers' samples among 40 samples (40%) at a cell count of 6.4±2.4 ($\text{Log}_{10}$(cell count)/g-feces).

Example 1

Production of Equol

To a daidzein-containing sorbose-PY medium (0.025% of daidzein, 1% of sorbose, 0.5% of peptone, 0.5% of trypticase peptone, 1% of yeast extract, 0.00005% of hemin, 0.0001% of vitamin K1, 0.05% of L-cystein hydrochloride, 0.0006% of $KH_2PO_4$, 0.0006% of $K_2HPO_4$, 0.0012% of NaCl, 0.0006% of $(NH_4)_2SO_4$, 0.00006% of $CaCl_2$, and 0.00006% of $MgSO_4$) (10 L), *Slackia* sp. YIT 11861 ($10^8$ cells/mL-medium) was added, and the cell-containing medium was incubated at 37° C. under a gas mixture ($N_2$:$H_2$:$CO_2$=88:7:5) for 96 hours. The culture solution was centrifuged (8,000×g, 15 minutes), and to the supernatant, an equivolume of diethyl ether was added. The mixture was sufficiently stirred and centrifuged again (1,000×g, 2 minutes), to thereby separate the mixture into two layers. Only the diethyl ether layer was recovered and dried at 40° C. under a flow of nitrogen to dryness, to thereby yield 2.4 g of equol.

Example 2

Production of Tablets

Ingredients shown in Table 4 were mixed. The mixture was granulated, dried, refined, and pelletized, to thereby yield tablets.

TABLE 4

| Formulation | (mg) |
|---|---|
| Dry cells of bacterium of the present invention[1] | 10 |
| Microcrystalline cellulose | 100 |
| Trehalose | 15 |
| Magnesium stearate | 0.5 |

TABLE 4-continued

| Formulation | (mg) |
|---|---|
| Methylcellulose | 12 |
| Daidzein | 25 |

[1] Produced by lyophilizing *Slackia* sp. YIT 11861 viable cells (containing $10^{10}$ viable cells/g).

Example 3

Production of Soft Drink

Ingredients shown in Table 5 were mixed through a routine method. The mixture was homogenized, to thereby yield a soft drink. The beverage was charged into a light-shielding brown bottle, and the bottle was sealed with an aluminum cap, followed by heat treatment.

TABLE 5

| Formulation | (g) |
|---|---|
| Dry cells of bacterium of the present invention[1] | 0.5 |
| Flavor | 0.8 |
| Citric acid | 0.2 |
| Erythritol | 2.5 |
| Lactitol | 2.5 |
| Water | 93.5 |

[1] Produced by lyophilizing *Slackia* sp. YIT 11861 viable cells (containing $10^{10}$ viable cells/g).

The invention claimed is:

1. An isolated microorganism having an ability of converting daidzein to equol in 24 hours at a rate of 50% or higher, wherein the microorganism is *Slackia* sp. YIT 11861 (FERM BP-11231).

2. The microorganism according to claim 1, which is derived from human feces and/or human digestive tract contents.

3. A food/beverage or pharmaceutical composition, comprising the microorganism according to claim 1.

4. The composition according to claim 3, which further comprises one or more species selected from among adonitol, arabinose, erythritol, galactose, lactitol, melezitose, trehalose, ribose, sorbose, xylose, inositol, and sorbitol.

5. The composition according to claim 3, which further comprises daidzein.

6. A method for producing equol, comprising contacting daidzein with an amount of the microorganism according to claim 1 effective to convert the daidzein to equol at a rate of 50% or higher.

* * * * *